(12) United States Patent
De Villiers

(10) Patent No.: US 11,795,141 B2
(45) Date of Patent: *Oct. 24, 2023

(54) COMPOSITION AND METHOD FOR TREATING UREA

(71) Applicant: CROMMELIN AGRICOATINGS PTY LTD, Rockingham (AU)

(72) Inventor: Hein De Villiers, Rockingham (AU)

(73) Assignee: CROMMELIN AGRICOATINGS PTY LTD, Rockingham (AU)

(*) Notice: Subject to any disclaimer, the term of this patent is extended or adjusted under 35 U.S.C. 154(b) by 0 days.

This patent is subject to a terminal disclaimer.

(21) Appl. No.: 17/585,785

(22) Filed: Jan. 27, 2022

(65) Prior Publication Data

US 2022/0144764 A1 May 12, 2022

Related U.S. Application Data

(63) Continuation of application No. 17/281,107, filed as application No. PCT/AU2019/051035 on Sep. 25, 2019, now Pat. No. 11,267,783.

(30) Foreign Application Priority Data

Oct. 2, 2018 (AU) ................................. 2018903720
Jul. 26, 2019 (AU) ................................. 2019902669

(51) Int. Cl.
*C07C 273/14* (2006.01)
*C05C 9/00* (2006.01)

(52) U.S. Cl.
CPC ............ *C07C 273/14* (2013.01); *C05C 9/005* (2013.01)

(58) Field of Classification Search
None
See application file for complete search history.

(56) References Cited

U.S. PATENT DOCUMENTS

| 3,535,376 | A | 10/1970 | Scheirer et al. |
| 10,093,590 | B2 | 10/2018 | Hayes |

(Continued)

FOREIGN PATENT DOCUMENTS

| GB | 1 214 448 | 12/1970 |
| GB | 1 217 106 | 12/1970 |
| WO | WO 2015/034375 | 3/2015 |

OTHER PUBLICATIONS

Examination Report dated Nov. 24, 2022 in Indian Application No. 202137014794.

(Continued)

*Primary Examiner* — Amy C Bonaparte
(74) *Attorney, Agent, or Firm* — Stephen J. Weyer, Esq.; Stites & Harbison, PLLC

(57) ABSTRACT

The present disclosure provides a composition for treating urea particles under ambient atmospheric conditions, a method for treating urea particles with the composition and to a fertiliser treated with the composition. The composition functions to reduce moisture induced agglomeration of treated urea particles compared to moisture induced agglomeration of untreated urea particles. The composition includes a solvent and a mixture of a first and a second aliphatic compound, each compound respectively comprising a selected $C_8$-$C_{14}$ saturated straight chain hydrocarbon a selected $C_{15}$-$C_{19}$ saturated straight chain hydrocarbon.

22 Claims, 8 Drawing Sheets

(56) References Cited

U.S. PATENT DOCUMENTS

| | | |
|---|---|---|
| 10,815,160 B2 | 10/2020 | Riaza Martinez et al. |
| 11,267,783 B2 * | 3/2022 | De Villiers ........... C07C 273/14 |
| 2016/0340267 A1 | 11/2016 | Hayes |
| 2018/0208516 A1 | 7/2018 | Riaza Martinez et al. |

OTHER PUBLICATIONS

Examination Report dated Dec. 15, 2022 in European Application No. 19868603.2.
Supplementary European Search Report for EP 19 86 8603 dated May 5, 2022.

* cited by examiner

| % | Compound Name | Chemical Formula | 2-D molecular model | 3-D molecular model |
|---|---|---|---|---|
| 1.6 | Methyl Myristate | $C_{15}H_{30}O_2$ |  |  |
| 22.3 | Methyl Palmitate | $C_{17}H_{34}O_2$ |  |  |
| 1.3 | Methyl Palmitoleate | $C_{17}H_{32}O_2$ |  |  |
| 0.6 | Methyl Heptadecenoate | $C_{18}H_{34}O_2$ |  |  |
| 10.0 | Methyl Stearate | $C_{19}H_{38}O_2$ |  |  |

| % | Compound Name | Chemical Formula | 2-D molecular model | 3-D molecular model |
|---|---|---|---|---|
| 43.5 | Methyl Oleate | $C_{19}H_{36}O_2$ |  | |
| 17.5 | Methyl Linoleate | $C_{19}H_{34}O_2$ |  |  |
| 2.8 | Methyl Linolenate | $C_{19}H_{32}O_2$ |  |  |
| 0.3 | Methyl Eicosenoate | $C_{21}H_{40}O_2$ |  | |

COMPOSITION AND METHOD FOR TREATING UREA

TECHNICAL FIELD

The present disclosure relates to a composition and method for treating urea.

More particularly, the present disclosure relates to a composition and method for forming a surface coating or barrier layer on solid urea particles to reduce agglomeration or clumping of the particles.

BACKGROUND

Urea, also known as carbamide or carbonyldiamide, is an organic compound with the chemical formula $CO(NH_2)_2$ having two amide groups attached to the sides of a carbonyl functional group. Solid urea is widely used in agriculture as a fertiliser providing a source of nitrogen and for this purpose is supplied as particles (granules or prills), normally having a size of about 1-4 mm in diameter and being generally spherical in shape.

Solid urea is highly hygroscopic and tends to absorb moisture from the environment when the ambient atmosphere is sufficiently humid, e.g. above 72.5% (30° C.). In storage this moisture uptake causes crystal bridges to form between abutting particles and this leads to the particles fusing and clumping together and, in severe cases, solid cake formation (as shown in FIGS. 1 and 3). The hygroscopic nature of urea reduces the flowability of the urea particles in humid conditions and leads to the inability to blend the urea granules with most other fertiliser grades. It also limits the dispersion of the urea particles through agricultural applicators, such as spreaders and air-seeders.

A further disadvantage is that urea cannot be blended with most other solid fertilisers such as NPK fertiliser (a three-component fertiliser providing nitrogen, phosphorus and potassium), AP fertiliser (Ammonium Phosphate), or SSP fertilisers (Single Superphosphate) without the urea lowering the blend's critical relative humidity (CRH)—the humidity at which the blend starts to absorb moisture. This problem is illustrated in FIGS. 5 and 7 wherein the moisture absorption and concomitant crystal bridge formation can be seen.

The above problems are known in industry and attempts have been made to provide solutions. However, almost all down-stream value added treatment of urea particles is performed under non-ambient conditions in manufacturing plants typically employing specialised pressure and temperature vessels. For example, U.S. Pat. No. 10,093,590 (WO2015/116301) discloses a method for treating fertilizer (including urea) wherein the urea is contacted with a liquid composition comprising organic solvents and/or petroleum distillates. However, many of the coating compositions disclosed in U.S. Pat. No. 10,093,590 are inherently dangerous as they contain flammable/combustible components—this is directly acknowledged in the disclosure. Furthermore, the coating process disclosed in U.S. Pat. No. 10,093,590 requires mixing of the urea and the coating composition for a relatively long time; the example given therein specifies mixing for at least 30 minutes and then baking thereof at a temperature of 60-70° C. for another 30 minutes. This coating process is thus limited in its general applicability and ease of application.

It is to be understood that, if any prior art publication is referred to herein, such reference does not constitute an admission that the publication forms a part of the common general knowledge in the art, in Australia or any other country.

SUMMARY OF THE DISCLOSURE

According to a first aspect of the disclosure, there is provided a composition for treating urea particles, the composition comprising water as a polar solvent;
  a first aliphatic compound comprising a saturated straight chain hydrocarbon selected from the group of $C_8$-$C_{14}$ hydrocarbons; and
  a second aliphatic compound comprising a saturated straight chain hydrocarbon selected from the group of $C_{15}$-$C_{19}$ hydrocarbons;
  wherein moisture induced agglomeration of urea particles treated with the composition under ambient atmospheric conditions is reduced compared to moisture induced agglomeration of untreated urea particles.

In one embodiment the water comprises between 10%-30% (w/w) of the composition.

The first aliphatic compound may include a compound of the formula

wherein
$R^1$ comprises hydrogen or a first terminal functional group;
$R^2$ comprises hydrogen or a second terminal functional group; and
n is 8 to 14.

The first and second terminal functional group may be selected from the group of hydroxyl, carboalkoxy and carboxyl functional groups, i.e. the first aliphatic compound may be selected from the group of alkanes, alcohols, esters and carboxylic acids. The first aliphatic compound may be an alcohol selected from the group of 1-octanol, 1-nonanol, 1-decanol, 1-undecanol, 1-dodecanol, 1-tridecanol, 1-tetradecanol. In one embodiment the first aliphatic compound is 1-dodecanol. The first aliphatic compound may be an ester selected from the group of octyl acetate and dodecyl acetate. The first aliphatic compound may be a carboxylic acid selected from the group of octanoic, nonanoic, decanoic, undecanoic, dodecanoic, tridecanoic acid. The first aliphatic compound may be a carboxylic acid ester selected from the group of methyl, ethyl, and propyl esters of any of the saturated, un-branched carboxylic acids as defined above.

The second aliphatic compound may be a compound of the formula

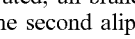

wherein
R comprises hydrogen or a carboxyl group; and
n is 15 to 19.

The second aliphatic compound may be a component of a mixed methyl ester, a palm methyl ester, a tallow methyl ester or similar. The mixed methyl ester may be selected from the group of a biodiesel, recycled cooking oils and recycled cooking fats.

The mixed methyl ester, the palm methyl ester or the tallow methyl ester may include
  30-40% (w/w) of the second aliphatic compound; and
  60-70% (w/w) of unsaturated hydrocarbons, branched chain hydrocarbons and aromatic hydrocarbons.

The composition may include
  15-20% (w/w) of the water;
  5-20% (w/w) of the first aliphatic compound; and
  60-80% (w/w) of a mixed methyl ester containing the second aliphatic compound.

The composition may include 0-1% (w/w) of an emulsifier or 0-2% (w/w) of a dispersing agent.

According to a second aspect of the disclosure, there is provided a method of treating urea particles, the method comprising the steps of
- a) dosing a supply of urea particles with an amount of a liquid composition effective for reducing moisture induced agglomeration of the urea particles, wherein the liquid composition includes
    water as a polar solvent,
    a first aliphatic compound comprising a saturated straight chain hydrocarbon selected from the group of $C_8$-$C_{14}$ hydrocarbons, and
    a second aliphatic compound comprising a saturated straight chain hydrocarbon selected from the group of $C_{15}$-$C_{19}$ hydrocarbons;
- b) mixing the urea particles and the liquid composition under ambient atmospheric conditions at a temperature of 15-40° C. and a humidity of 30-90% to promote coating of the urea particles with the liquid composition, whereby the liquid composition is configured to form a barrier layer comprising a urea clathrate that at least partially encloses the urea particles; and
- c) allowing the urea clathrate to cure under the ambient atmospheric conditions for a time period of 30-120 seconds, thereby forming treated urea particles.

The liquid composition may be a composition for treating urea particles as described in the first aspect of the disclosure.

The method may comprise the step of selectively altering the ratio between the water, the first aliphatic compound and the second aliphatic compound, thereby to adjust a rate of curing of the urea clathrate.

The urea particles may be dosed with the liquid composition at a rate of about 5-15 kg of liquid composition per 1000 kg of urea particles. In one embodiment the urea particles are dosed with the liquid composition at a rate of about 7.5-10 kg of liquid composition per 1000 kg of urea particles. In another embodiment, when the urea particles are to be blended with other solid fertilisers, the urea particles are dosed with the liquid composition at a rate of about 10-15 kg of liquid composition per 1000 kg of urea particles.

The composition may be configured that the water dissolves an outer layer of the urea particles enabling the dissolved urea molecules to form the urea clathrate with the first aliphatic compound and/or with the second aliphatic compound.

The urea clathrate may be allowed to cure for a time period of 30-120 seconds under ambient atmospheric conditions.

The method may include adding selective trace elements or micro particles to the urea particles during step (a) or step (b) so that the treated urea particles formed during step (c) include selective trace elements or micro particles entrapped within the urea clathrate. The trace elements or micro particles are not limited to, but can typically be selected from the group of
- nano-particles of zinc oxide, copper oxide, lime, elemental sulphur;
- humic/fulvic acid;
- lignins
- redispersable polymer powders; and
- (n-Butyl) Thiophosphoric Triamide (NBPT).

The urea particles may be treated after being manufactured, after being off-loaded from a bulk transport, or prior to being distributed or bagged for distribution to down-chain wholesalers, retailers or consumers.

According to a third aspect of the disclosure, there is provided a fertiliser comprising
- urea particles; and
- a barrier layer at least partially enclosing the urea particles, wherein the barrier layer comprises a urea clathrate formed by urea molecules at least partially enclosing a first aliphatic compound comprising a saturated straight chain hydrocarbon selected from the group of $C_8$-$C_{14}$ hydrocarbons and by urea molecules at least partially enclosing a second aliphatic compound comprising a saturated straight chain hydrocarbon selected from the group of $C_{15}$-$C_{19}$ hydrocarbons;
- wherein moisture induced agglomeration of the fertiliser composition is reduced compared to moisture induced agglomeration of the urea particles alone.

The barrier layer may be formed by treating the urea particles with a composition as described in the first aspect of the disclosure.

The fertiliser may include a blend of the urea particles together with other fertiliser types and wherein the critical relative humidity of the blend remains substantially unchanged compared to the critical relative humidity of the other fertiliser types alone.

BRIEF DESCRIPTION OF DRAWINGS

The above and other features will become more apparent from the following description and with reference to the accompanying schematic drawings. In the drawings, which are given for purpose of illustration only and are not intended to be in any way limiting.

DETAILED DESCRIPTION

Figure 1:
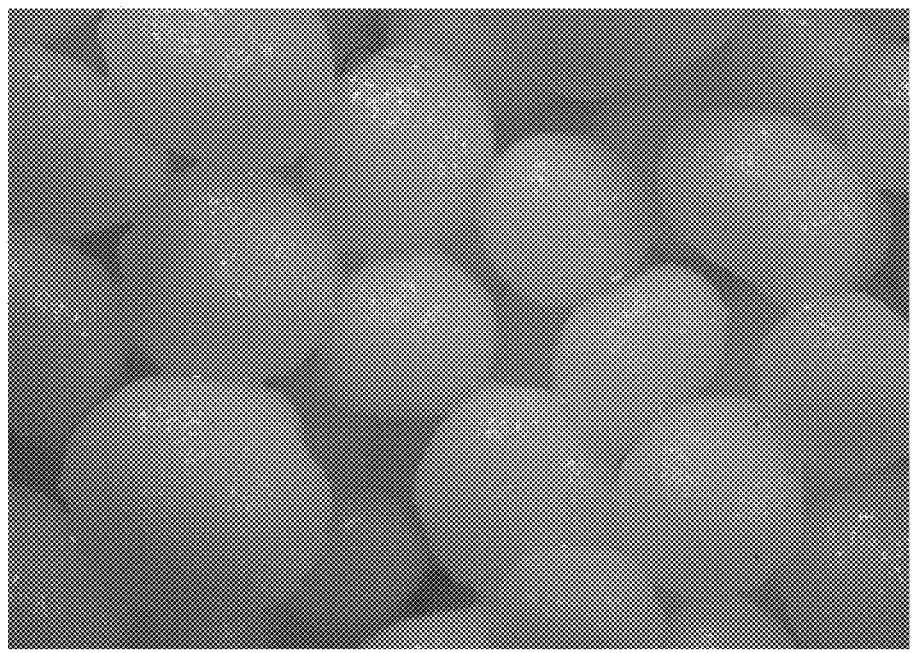
FIG. 1 is a photograph of a sample of untreated urea particles that have been exposed for 16 hours to an atmosphere at a temperature of 20° C. and 80% humidity.

The present disclosure relates to a composition for treating urea under ambient atmospheric conditions to form a surface coating or barrier layer on solid urea particles (such as prills or granules), wherein moisture induced clumping and agglomeration of the urea particles treated with the composition is reduced compared to moisture induced clumping and agglomeration of untreated urea particles. The composition also assists in reducing physical breakdown of the urea particles with a concomitant reduction in the prevalence of urea dust formation. The present disclosure also provides a method of treating urea particles with the composition.

When the composition is applied to the urea particles under ambient atmospheric conditions, the composition dissolves a surface layer of the urea particles allowing the dissolved urea molecules to form a urea-hydrocarbon clathrate (also commonly referred to as an inclusion compound or inclusion adduct), wherein the urea molecules form a host crystal structure that has channel voids therein, and in which channel voids an aliphatic tail of an aliphatic compound can be trapped as a guest.

The formation of the urea-hydrocarbon clathrate (hereinafter referred to as the urea clathrate) is dependent on the molecular structure of the adductable hydrocarbons and also particularly on the temperature at which the clathrate is to form—both of these variables impact on the length of time required for the clathrate to form. During formation of the clathrate the urea molecules reform and recrystallise with the urea molecules held together by hydrogen bonds in the form of a hexagonal lattice which has long connected channel voids. The cross-sectional width of the channel voids is about five to six Angstroms, which corresponds to the width of many straight chain hydrocarbons. The clathrate is formed by the hydrocarbons being trapped in these channel voids. Because of weak van der Waals forces between the urea molecules and the molecules of the hydrocarbons, the hydrocarbons stabilize the hexagonal lattice of the clathrate. The molecules of the hydrocarbons are not included in any particular spatial arrangement.

Generally, any hydrocarbon having a saturated straight chain (unbranched) aliphatic tail with more than four carbons can form a urea clathrate. When the aliphatic tail is short, i.e. $C_5$ to $C_7$, the urea clathrate generally forms very quickly (typically within seconds or under one minute) but is unstable and the solution must be cooled for the clathrate to remain intact (typically to temperatures <5° C.). The reason for this instability is because these shorter chain molecules are relatively volatile, which makes them less likely to stay intact within the channel voids. When the aliphatic tail is mid-length, i.e. $C_8$ to $C_{14}$, a stable urea clathrate is generally able to form at ambient temperatures (around 15-40° C., normally being around 15-30° C. and typically being about 25° C.) within a period of 1-10 minutes—these compounds are referred to hereinafter as being "readily adductable". When the aliphatic tail is still mid-length but slightly longer, i.e. $C_{15}$ to $C_{19}$, a stable urea clathrate is generally able to form at ambient temperatures within a period of 10-240 minutes—these compounds are referred to hereinafter as being "semi-readily adductable". Lastly, when the aliphatic tail is very long, i.e. $C_{20}$, a stable urea clathrate generally only forms at ambient temperatures after a period of >2 hours—these compounds are referred to below as being "non-readily adductable".

As the length of the aliphatic tail of the hydrocarbon increases, the stability of the urea clathrate increases. This is because the channel voids in the host crystal structure are not inherently stable but become stabilized by the presence of the guest aliphatic compound. The host crystal structure has a stronger affinity for longer aliphatic compound chains. In the absence of a guest compound to provide the necessary stability, the host crystal structure will revert to its original stable tetragonal linked crystal structure which does not have any channel voids.

Mono- and poly-unsaturated hydrocarbons, branched chain hydrocarbons and most aromatic hydrocarbons are not likely to form a suitable clathrate with urea molecules under atmospheric conditions—these compounds are referred to below as being "non-adductable". However, it should be appreciated that some aromatic hydrocarbons may be able to form a urea clathrate provided the aromatic hydrocarbon contains a long enough straight chain substituent. Similarly, in some instances also mono- and poly-unsaturated hydrocarbons may be able to form a urea clathrate if their structure is suitable and their double and triple bonds are located towards one end of the hydrocarbon chain with an opposed end of the chain being unsaturated and sufficiently long to enter the channel voids. As an example of this, a urea clathrate can form with the aromatic compound octadecyl benzene, which contains a benzene ring connected to a sufficiently long straight chain hydrocarbon substituent. Conversely, benzene alone, without any substituent, does not form a urea-hydrocarbon clathrate—as is the case with most to all other aromatic un-substituted compounds.

The composition of the present disclosure includes a solvent, a readily adductable component, a semi-readily adductable component and optionally a non-readily adductable component. The readily adductable component includes a first aliphatic compound having a terminal functional group and an aliphatic tail comprising a saturated straight chain hydrocarbon selected from the group of $C_8$-$C_{14}$ hydrocarbons. The semi-readily adductable component includes a second aliphatic compound having a terminal functional group and an aliphatic tail comprising a saturated straight chain hydrocarbon selected from the group of $C_{15}$-$C_{19}$ hydrocarbons. The non-readily adductable component includes a third aliphatic compound having a terminal functional group and an aliphatic tail comprising a saturated straight chain hydrocarbon selected from the group of $\geq C_{20}$ hydrocarbons.

The composition is selected to comprise a suitable mixture ratio of the solvent, the readily adductable, the semi-readily adductable and any non-readily adductable components so that when applied to the urea particles the urea clathrate forms within a desired curing time.

Figure 10:
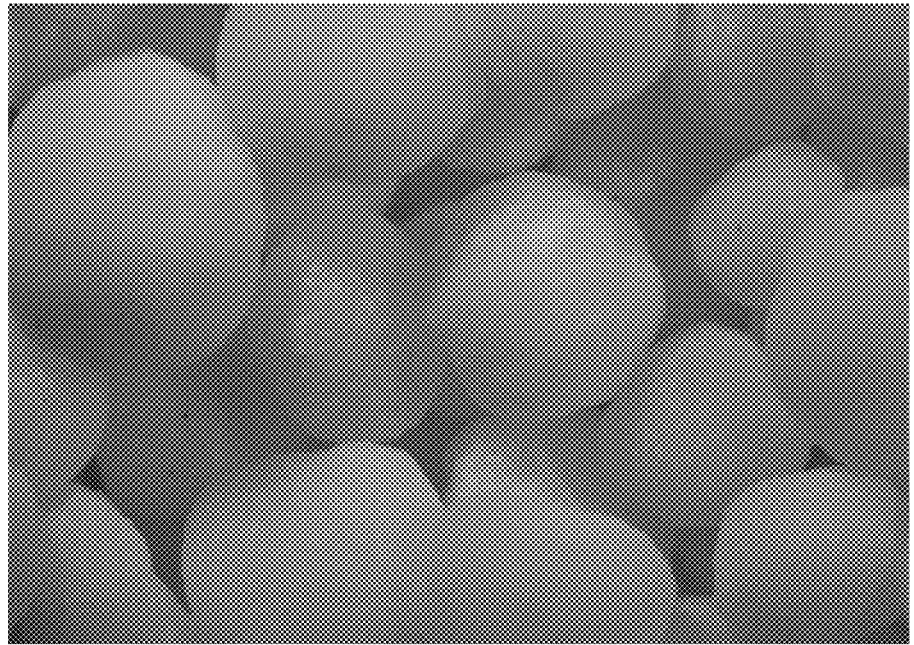
FIG. 10 is a photograph of a sample of treated urea particles showing a defect of urea clathrate flakes due to improper integration of the urea clathrate onto the surface of the urea particles.

If the curing time is too short, the urea clathrate forms too quickly and does not integrate properly onto the surface of the urea particles. This results in urea clathrate flakes forming on the surface of the urea particles which flakes are easily dislodged from the urea particles—either due to frictional contact with other urea particles or during subsequent handling. An example of urea particles with such urea clathrate flakes is shown in FIG. 10. Typically, such a short curing time is found if the composition comprises a mixture ratio having too large a percentage of $C_8$-$C_{14}$ hydrocarbons.

Conversely, if the curing time is too long, the urea particles attract moisture and experience moisture induced clumping and agglomeration before the barrier layer can form. This results in the barrier layer eventually forming around the agglomerated urea particles, which again hinders handling and dispersion of the urea particles. Typically, such a long curing time is found if the composition comprises a mixture ratio having too large a percentage of $C_{15}$-$C_{19}$ hydrocarbons.

The solvent is a polar solvent suitable for dissolving a surface layer of the urea particles. Although there are many polar solvents suitable for this purpose, it will be appreciated that in the context of this disclosure (as will be exemplified below) inducing the formation of the urea clathrate is aimed at forming a barrier layer surrounding the urea particles to reduce clumping and lump formation of the urea particles. The barrier layer formed by the composition is susceptible to dissolution in the presence of excess solvent as it would break down the urea clathrate, which would negate the purpose of applying the composition to the urea particles. Accordingly, the solvent is selected as a non-hygroscopic polar solvent to avoid ambient moisture being attracted and absorbed by the barrier layer and in the exemplary example the solvent is water. Water is an inert polar solvent and therefore has the advantage that it does not interfere with changes in the molecular structure of the urea while the clathrate is being formed. A further advantage of using water as the solvent is that water is not flammable or combustible.

The readily adductable component and semi-readily adductable component are aliphatic compounds having a terminal functional group and an aliphatic tail comprising a saturated straight chain hydrocarbon selected from the group of $C_8$-$C_{19}$ hydrocarbons. In the exemplary examples a coco methyl ester and a lauryl alcohol, being $C_{12}$ dominant hydrocarbons, are selected as the readily adductable aliphatic compounds.

In alternative embodiments, the readily and semi-readily adductable aliphatic compound may be selected from alkanes, alcohols, esters and carboxylic acids, provided the selected compound has an aliphatic tail with the molecular structure of a $C_8$-$C_{19}$ saturated straight chain hydrocarbon.

For example, suitable alcohols can include 1-octanol, 1-nonanol, 1-decanol, 1-undecanol, 1-dodecanol (lauryl alcohol), 1-tridecanol, and 1-tetradecanol. Examples of suitable esters are octyl acetate and dodecyl acetate. Examples of suitable carboxylic acids are octanoic, nonanoic, decanoic, undecanoic, dodecanoic, tridecanoic acid. Alternative esters which may be used are the methyl, ethyl, and propyl esters of saturated, un-branched carboxylic acids, for example those of the aforementioned carboxylic acids.

In the exemplary example the non-readily adductable component is obtained from a mixed/fatty acid methyl ester. In other embodiments the non-readily adductable component can be obtained from a palm methyl ester or a tallow methyl ester. Mixed methyl esters typically include a variety of different hydrocarbons and some of these will be adductable, whereas others will be non-adductable. A mixed methyl ester obtained from biodiesel or recycled cooking oils and fats typically includes about 30-40% adductable hydrocarbons whereas the rest largely comprises non-adductable hydrocarbons. Typically, these adductable hydrocarbons are $C_{15}$-$C_{19}$ hydrocarbons. The non-adductable hydrocarbons generally include molecules with aliphatic tail being too long (>$C_{20}$), mono- and poly-unsaturated hydrocarbons or aromatic hydrocarbons. Although the non-adductable hydrocarbons do not partake in the clathrate formation process, they do play a role in integrating the urea clathrate onto the surface of the urea particles.

Figure 12:
FIGS. 12A and 12B are tables listing exemplary examples of mixed methyl esters having various structures.
Figure 12:
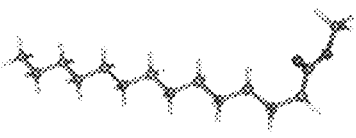
Figure 12:
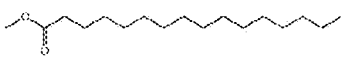
Figure 12:
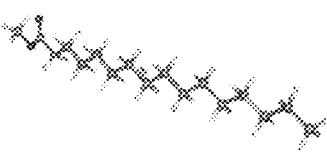
Figure 12:
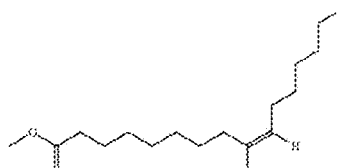
Figure 12:
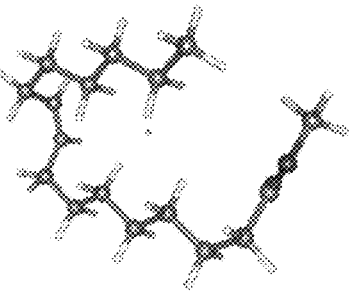
Figure 12:
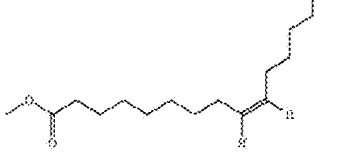
Figure 12:
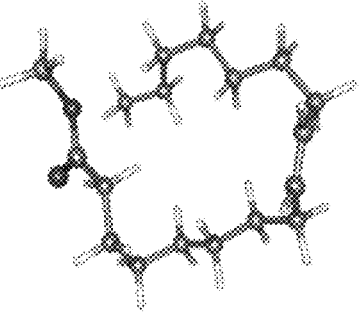
Figure 12:
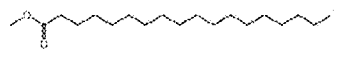
Figure 12:
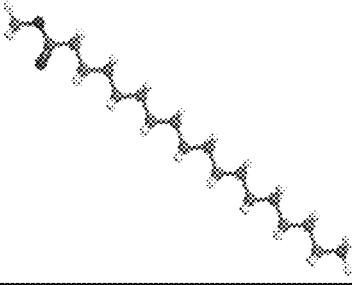
Figure 12:
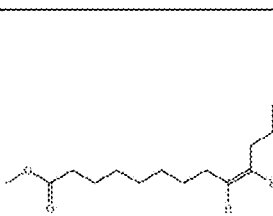
Figure 12:
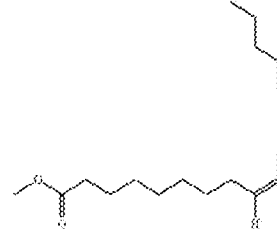
Figure 12:
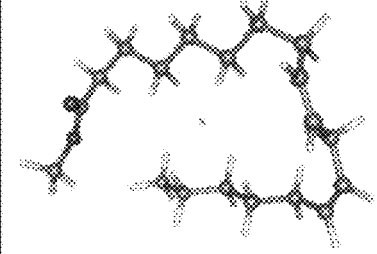
Figure 12:
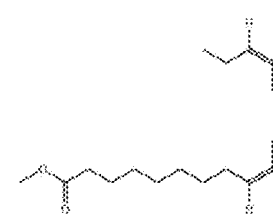
Figure 12:
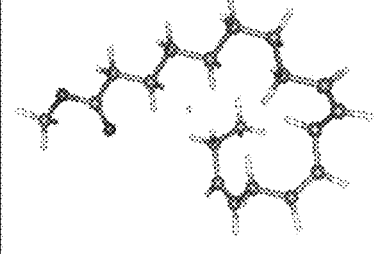
Figure 12:
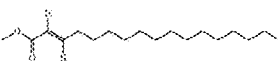

Exemplary examples of the mixed methyl esters have has the following composition: various composition forms, chemical formula and structures are shown in the tables of FIGS. 12A and 12B.

It is clear to see that the majority of the compounds are branched hydrocarbons making them unsuitable for forming a urea clathrate. There are only three viable compounds in the mixed methyl ester that are suitable for forming a urea clathrate, namely; methyl myristate, methyl palmitate and methyl stearate. These compounds make up about 34% of the mixed methyl ester (being semi-adductable hydrocarbons).

The exemplary embodiment of the composition includes
15-20% (w/w) water as the solvent component;
5-20% (w/w) a $C_8$-$C_{14}$ aliphatic hydrocarbon straight chain mixture as the readily adductable component; and
60-80% (w/w) mixed methyl ester containing the semi-readily adductable and the non-readily adductable components.

The volume of solvent used in the clathrate formation can vary between 10-30% of the composition. However, the most favourable results have been obtained with the solvent being between 15-20%. Ideally the volume of solvent is selected to have just enough for dissolving the surface layer of the urea particles to a desired depth and also so that there is not an excess of solvent that needs to be evaporated at ambient conditions. The clathrate layer is only completely formed or cured once all of the solvent has been evaporated or incorporated into the crystal structure of the urea clathrate.

Normally, if the solvent comprises less than 15% of the composition, then not enough of the surface of the urea particles is dissolved and there is an insufficient volume of urea able to react with the available adductable hydrocarbons to form the barrier layer. The insufficient dissolving of urea particles is indicative of a composition which includes too much of either the mixed methyl ester or of $C_{12}$-$C_{14}$ straight chain hydrocarbons in the readily adductable content. This ultimately leads to the urea particles being coated with an unstable or low performance oily hydrocarbon layer instead of the higher performing urea clathrate layer obtained by sufficient dissolved urea particulate matter being in the presence of sufficient adductable content. The urea particles coated with the oily layer can and most probably will lead to clumping and agglomeration of the urea particles.

Normally, if the solvent comprises more than 20% of the composition, then an excess amount of the surface of the urea particles is dissolved and not all the dissolved urea will react with the available adductable hydrocarbons. This tends to result in the urea clathrate being dispersed within the solvent and resulting in the clathrate not integrating properly onto the surface of the urea particles until most to all of the solvent has evaporated, which could be time consuming at ambient conditions. Furthermore, such a poorly integrated urea clathrate can also result in parts of the urea clathrate being loosely deposited onto the surface of the urea particles, making them prone to becoming dislodged during subsequent handling of the urea particles, which ultimately leads to dust formation. Another potential problem in utilising an excess of solvent is that it may lead to the growth of urea crystals from the urea particles as the dissolved urea subsequently sets (cures). These crystals can sometimes pierce the urea clathrate barrier layer and thereby provide a pathway for moisture being attracted to the urea particle surface which can again cause moisture induced agglomeration of the urea particles. In some cases these crystals break free from the urea particles and lead to dust formation.

In general, if the ratio of total available adductable components to the solvent component is between 1:1.5 and 1:2.5, preferably being at least 1:2, then the composition results in the formation of a urea clathrate layer displaying favourable boundary protection properties.

As mentioned above, by varying the ratio of the readily adductable hydrocarbons and the semi-readily hydrocarbons (typically obtained from the mixed methyl ester) it is possible to adjust the length of time for the urea clathrate boundary layer to cure after application of the composition to the urea particles.

If the readily adductable hydrocarbons comprises around 5-10% of the composition, the rate of clathrate layer formation is borderline slow, and when comprising less than 5% of the composition the layer forming is restrained resulting in a tendency of the urea particles experiencing moisture induced agglomeration before the barrier layer is formed. If the readily adductable hydrocarbons comprises more that 20% of the composition, then the urea clathrate forms too quickly and forms improperly integrated flakes on the surface of the urea particles that have a tendency to become dislodged from the urea particles, i.e. leaving the urea particles without a barrier layer, and again allowing the urea particles to experience moisture induced agglomeration. The dislodged flakes also lead to urea dust formation.

The semi-readily adductable and the non-readily adductable hydrocarbon components impact the quality and stability of the urea clathrate that is formed and also its integration onto the surface of the urea particle. This is due to these hydrocarbons slowing down the curing time of the urea clathrate.

If the combination of the semi-readily adductable and the non-readily adductable hydrocarbons comprises less than 60% of the composition, then a low-quality urea clathrate forms too quickly and is improperly integrated on the surface of the urea particles leading to the formation of flakes. If the combination of these hydrocarbons comprises more that 80% of the composition, then the urea clathrate forms too slowly and the urea particles tend to experience moisture induced agglomeration before the barrier layer is sufficiently formed.

The composition can optionally include an emulsifier, surfactant or oil dispersant to assist the readily adductable hydrocarbons and the mixed methyl ester to disperse within the water solvent to form an emulsion. However, in some instances the emulsifier may interfere with the formation of the clathrate and thus the presence of the emulsifier should be limited to 0-1% (w/w) of the composition. Suitable emulsifiers for use include the commercially available Berol 9985. The presence of a dispersing agent is required if additional nutritional components (usually supplied in powdered form) are to be added. The dispersing agent is added at 0-2% (w/w) of the composition. Suitable dispersing agents for use include any of the polyether polymers (PEG) such as PEG 400 MO (Palm or Tallow based).

In use, the composition is applied to the urea particles via a drip bar or spray nozzles in a suitable granular fertiliser mixer, such as a paddle mixer, ribbon blender, rotating drum, coating cylinder or auger. The urea particles are mixed by being tumbled or rolled together with the composition to promote dispersion of the composition between the urea particles and to achieve a good surface covering over the urea particles. The composition is applied at a rate of 5-15 kg composition per 1000 kg urea particles and this is intended to achieve about a 90-95% surface coverage of the urea particles.

When the composition is being applied primarily for providing an anti-caking layer on urea particles, the composition is normally applied to the urea at a rate of about 5-10 kg, typically at about 7.5 kg, composition per 1000 kg urea particles.

When the urea particles are to be blended with other solid granular fertilisers such as NPK or SSP fertilisers, the composition is normally applied to the urea at a rate of about 10-15 kg, typically at about 12.5 kg, composition per 1000 kg of urea particles. After being so treated with composition, the urea particles are then blended with the other fertilisers.

In a practical application for bulk storage or stockpiling, it is envisaged that the composition will be applied to the urea particles shortly after these are manufactured or are off-loaded to a warehouse facility from a bulk transport, e.g. a ship or railcar. Typically, the composition will be applied immediately prior to the urea particles being blended with other types of fertiliser or prior to being bagged and or distributed to down-chain wholesalers, retailers or consumers.

Due to the handling requirements when bagging the urea particles, the composition is applied to the urea particles under ambient atmospheric conditions, i.e. at a temperature of about 15-40° C. and at 30-90% humidity. Normally the composition will be maintained at a temperature of around 15-30° C. and typically being at a temperature about 25° C. During application, the composition is to be maintained at a temperature being at least higher than a cloud point of the composition, i.e. at a temperature above a highest cloud point temperature of the respective components of the composition. However, the treated urea particles need to cure sufficiently quickly after application of the composition so that they are sufficiently dry by the time the treated urea particles are bagged or loaded into a truck. Typically, this requires the treated urea particles to cure in such a way as to be touch-dry or hand-dry within two minutes, typically for a time period of 30-120 seconds under ambient atmospheric conditions. In some situations, the requisite curing time is reduced to under ninety seconds. Yet in other situations the preferred curing time should be 45-75 seconds.

It should be noted that the abovementioned warehouse facilities often do not have drying equipment available (such as heaters or fans) and therefore the curing of the urea clathrate layer also occurs under ambient conditions. Although the urea clathrate is not fully cured by the time the treated urea particles are touch-dry, further curing will occur in the bags and the clathrate will fully cure within 2-4 hours after application of the composition.

When the composition is applied to the urea particles in the mixer, the water dissolves the outer surface layer of the urea particles. The presence of the readily adductable hydrocarbons result in a fast formation of a partial urea clathrate layer that cures so that the treated urea particles become touch dry within the requisite time. Thereafter, the presence of the semi-readily adductable hydrocarbons result in the slower formation of the fully formed quality urea clathrate layer over the following few hours. The urea clathrate layer partially covering the surface of the urea particles provides a physical barrier that limits the surface contact between abutting urea particles. This barrier reduces the formation of the crystal bridges and results in urea particles having better handling and flowability, reduced clumping (especially under humid conditions) and reduced dust formation. The treated urea particles can be combined with other types of fertilisers without greatly lowering the critical relative humidity of the resultant fertiliser blend.

The urea clathrate layer does not modify the properties of the urea as a fertiliser. For example, the clathrate layer does not provide a barrier to moisture, such that moisture uptake by the treated urea particles is not prevented and does not affect any controlled release rate of the nitrogen from the urea particles. Thus, the urea particles are still able to dissolve when immersed in water or dispersed in soil so that the release properties of the treated urea particles remain substantially the same as untreated urea particles. For clarity, when the treated urea particles are brought into contact with water, the clathrate dissolves and releases the aliphatic, straight-chain compound. Since the aliphatic compound is present in such small quantities its presence in the fertiliser does not affect the working of the urea fertiliser and does not negatively affect any agricultural produce to which the urea fertiliser is applied.

As mentioned above, the clathrate layer formed on the urea particles reduces the absorption of moisture by the urea particles by providing a protective barrier partially surrounding the urea particles. The protective barrier provides a good foundation for the further application of additional coatings to be added to the urea particles, for example a secondary coating of selective trace elements.

In some embodiments, these trace elements or micro particles may be integrally provided within the boundary layer formed by the urea clathrate and trapped in place as the urea clathrate cures. For example the trace elements or micro particles are not limited to, but can typically be selected from the group of:

nano-particles of zinc oxide, copper oxide, lime, elemental sulphur;
humic/fulvic acid;
lignins
redispersible polymer powders, such as styrene acrylic; and
(n-Butyl) Thiophosphoric Triamide (NBPT) or similar molecules.

Figure 2:
FIG. 2 is a photograph of a sample of treated urea particles that have been exposed for 16 hours to an atmosphere at a temperature of 20° C. and 80% humidity.
Figure 3:
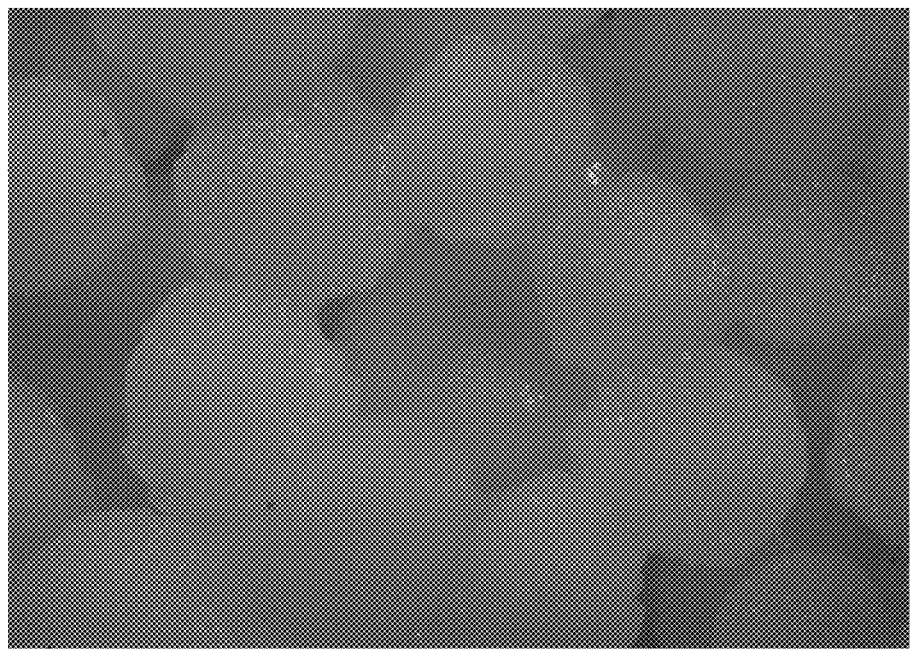
FIG. 3 is a photograph of a sample of untreated urea particles that have been exposed for four days to an atmosphere at a temperature of 20° C. and 80% humidity.
Figure 4:
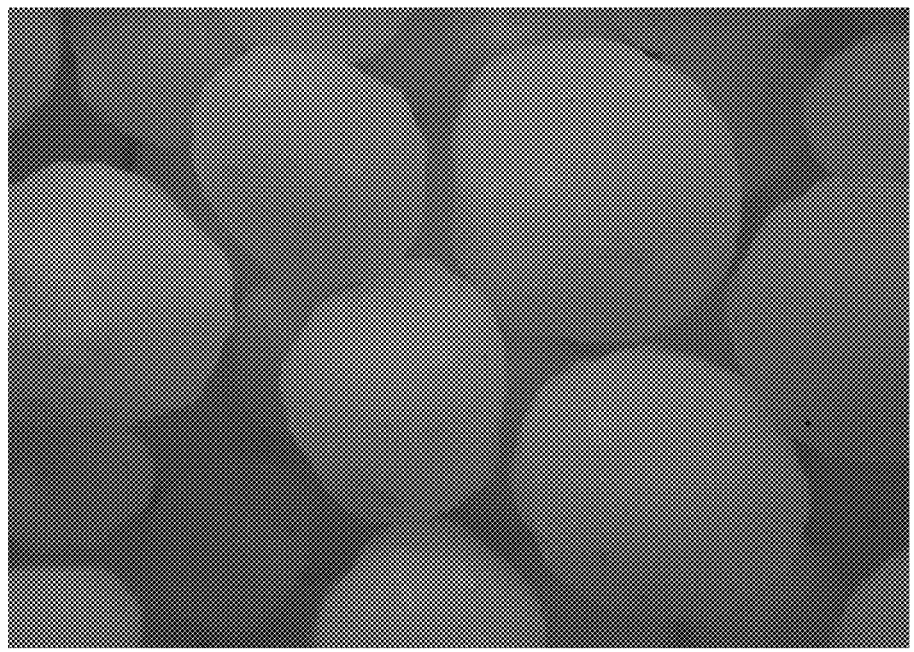
FIG. 4 is a photograph of a sample of treated urea particles that have been exposed for four days to an atmosphere at a temperature of 20° C. and 80% humidity.

The advantages and protective effect of the treated urea particles can be clearly seen by a simple visual comparison between untreated urea particles (FIG. 1) and treated urea particles (FIG. 2). In both cases the urea particles have been exposed for 16 hours to an atmosphere at a temperature of 20° C. and 80% humidity. FIG. 1 clearly displays the moisture absorption on the particles and the concomitant crystal bridge formation, whereas in FIG. 2 neither of these are present. The moisture absorption and crystal bridge formation are even more prevalent when the urea particles have been exposed to the same atmospheric conditions for four days, wherein FIG. 3 shows untreated urea particles and FIG. 4 shows treated urea particles.

Figure 5:
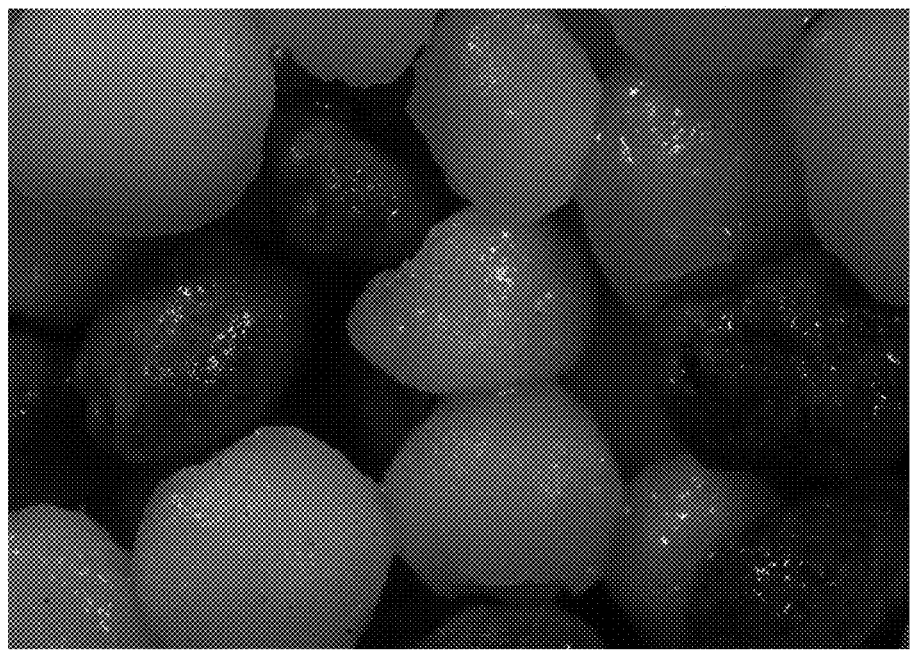
FIG. 5 is a photograph of a sample of a fertiliser blend of untreated urea particles (light particles) and single superphosphate fertiliser particles (dark particles), wherein the blend has been exposed for 16 hours to an atmosphere at a temperature of 20° C. and 80% humidity.
Figure 6:
FIG. 6 is a photograph of a sample of a fertiliser blend of treated urea particles (light particles) and single superphosphate fertiliser particles (dark particles), wherein the blend has been exposed for 16 hours to an atmosphere at a temperature of 20° C. and 80% humidity.

A further example of the protective effect of the treated urea particles is shown in FIGS. 5 and 6, which respectively show an untreated fertiliser blend (FIG. 5) and a treated fertiliser blend (FIG. 6). In both cases the fertiliser blend includes urea particles (light particles) and SSP fertiliser particles (dark particles) that have been exposed for 16 hours to an atmosphere at a temperature of 20° C. and 80% humidity. FIG. 5 clearly displays the moisture absorption on the particles and the concomitant crystal bridge formation, whereas in FIG. 6 neither of these are present.

Figure 7:
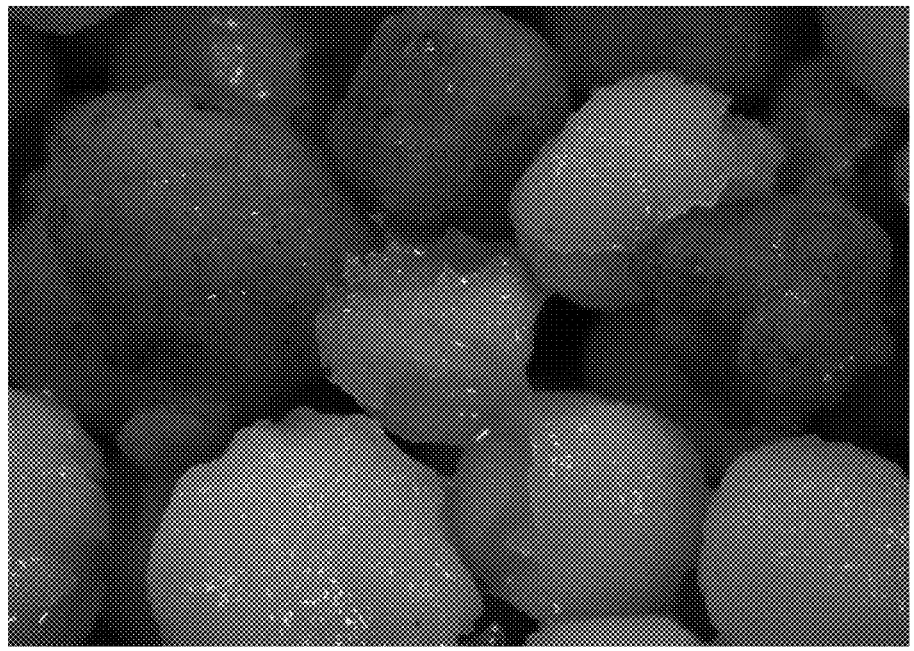
FIG. 7 is a photograph of a sample of a fertiliser blend of untreated urea particles (light particles) and monoammonium phosphate fertiliser particles (dark particles), wherein the blend has been exposed for 16 hours to an atmosphere at a temperature of 20° C. and 80% humidity.
Figure 8:
FIG. 8 is a photograph of a sample of a fertiliser blend of treated urea particles (light particles) and monoammonium phosphate fertiliser particles (dark particles), wherein the blend has been exposed for 16 hours to an atmosphere at a temperature of 20° C. and 80% humidity.
Figure 9:
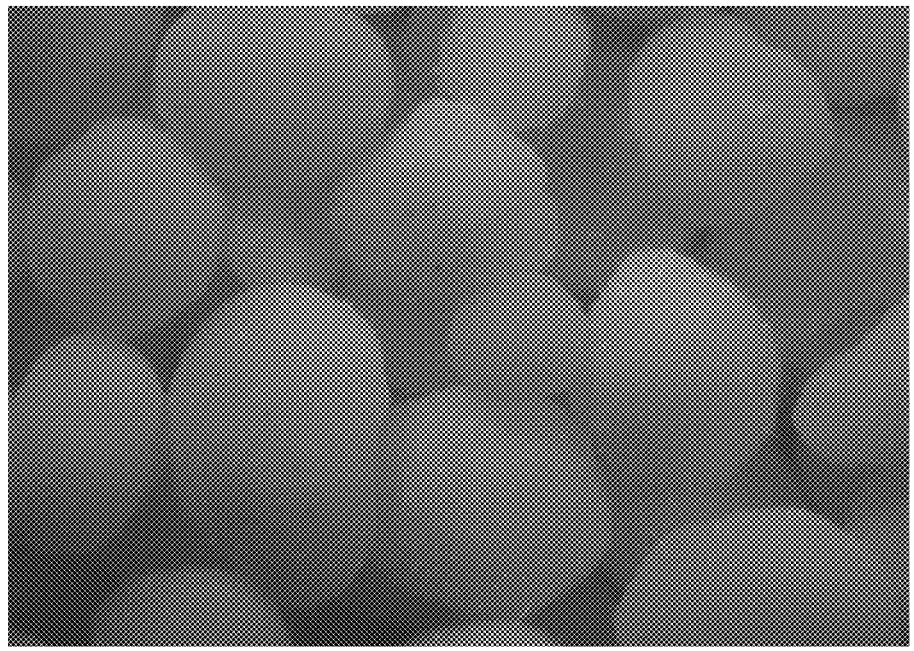
FIG. 9 is a photograph of a sample of treated urea particles showing a defect of crystal growth from the urea particles due to an excess of solvent.

A further example of the protective effect of the treated urea particles is shown in FIGS. 7 and 8, which respectively show an untreated fertiliser blend (FIG. 7) and a treated fertiliser blend (FIG. 8). In both cases the fertiliser blend includes urea particles (light particles) and MAP (monoammonium phosphate) fertiliser particles (dark particles) that have been exposed for 16 hours to an atmosphere at a temperature of 20° C. and 80% humidity. Again, FIG. 7 clearly displays the moisture absorption on the particles and the concomitant crystal bridge formation, whereas in FIG. 8 neither of these are present.

The morphological changes in the structure of the urea particles during formation of the urea clathrate may be observed through various techniques, such as optical microscopy, X-ray diffraction, Fourier-Transform infrared spectroscopy and Raman spectroscopy. For example, optical spectroscopy may reveal regions of the urea particle that are coated or uncoated. Raman spectroscopy may be used to detect the formation of the urea clathrate as described above, as this technique can distinguish between urea compounds in a tetragonal or hexagonal state, with the hexagonal state indicating that urea is present as a clathrate. X-ray diffraction studies or infrared spectroscopy may also be used to confirm the presence of urea in its hexagonal state and thus the formation of the urea clathrate, with characteristic diffraction peaks (for X-ray diffraction) and signals at characteristic wavenumbers (for infrared spectroscopy) observed in parts of a urea granule confirmed by other techniques to contain the clathrate. Thus, the above techniques may be used to characterise and detect urea particles treated according to a process of the present disclosure.

Figure 11:
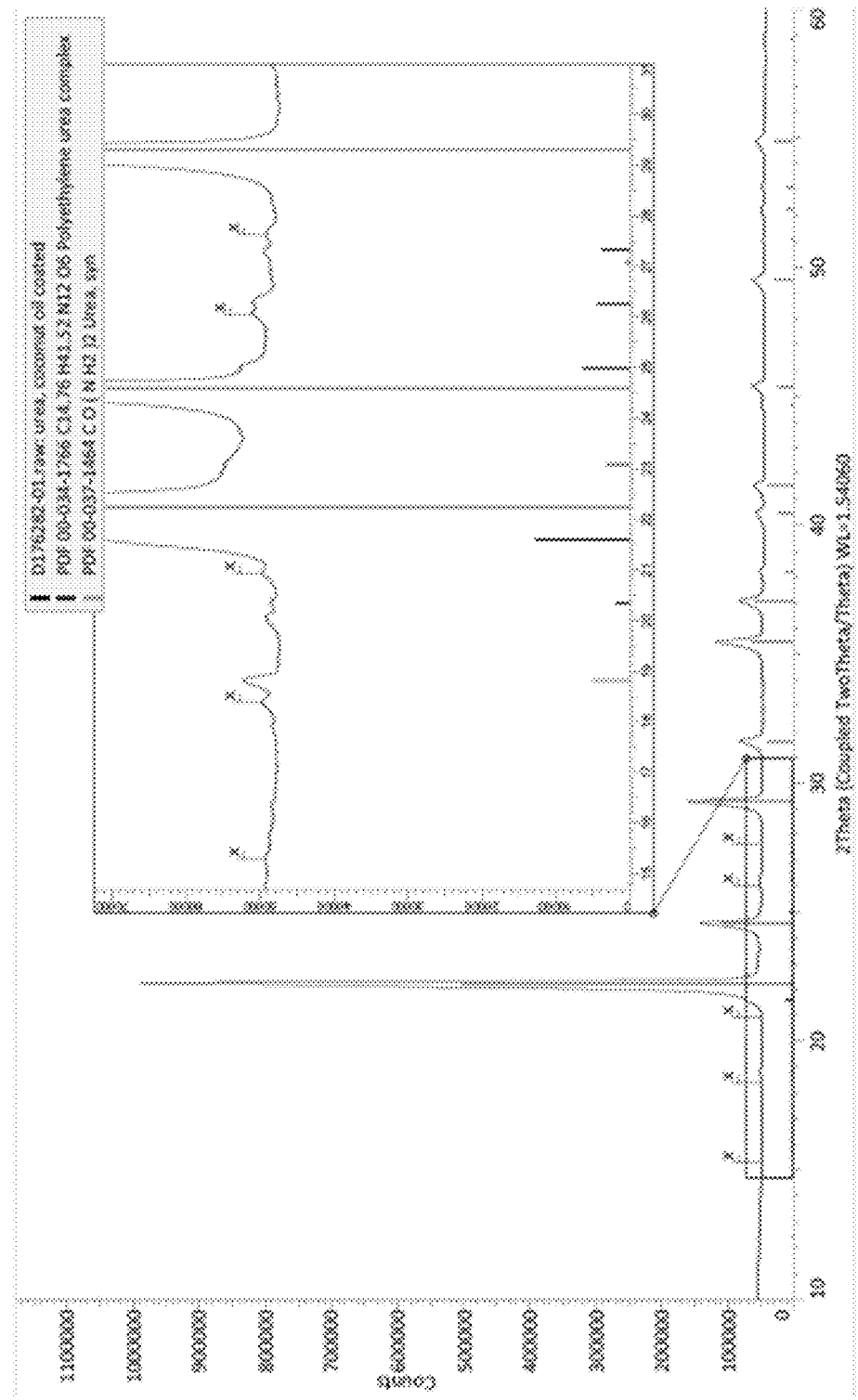
FIG. 11 shows an X-ray diffraction pattern of a urea particle treated with one example of the composition containing coconut oil and the major diffraction lines from the library database for both urea and a polyethylene urea complex.

FIG. 11 shows the X-ray diffraction (XRD) pattern of a urea particle treated with one example of the composition containing coconut oil and also the major diffraction lines from the XRD library database for both urea and a polyethylene urea complex. Crystalline phases were identified against ICDD-JCPDS database references. The major diffraction peaks for the sample align with the diffraction lines expected for urea. There are also clear matches for the smaller diffraction peaks that align with those for known hydrocarbon inclusion compounds, i.e. the expected peaks for a polyethylene urea complex that exhibits the same hexagonal crystal structure. These diffraction lines are also in agreement with the observations in Smith (see Smith AE (1952), The crystal structure of the Urea-Hydrocarbon Complexes, Acta Cryst., 5, 224-235).

Examples of Composition Mixtures

The following additional examples of composition mixtures are illustrative of the above description and should not be construed as limiting in any way the general nature of the disclosure of the description throughout this specification.

Example 1

It may be desired to form a strong urea clathrate that does not need to be fully formed in a very short period of time. This is accomplished with a composition containing a smaller percentage of the shorter chain aliphatic compounds along with a much larger percentage of the longer chain aliphatic compounds. In this example the composition typically comprises (w/w):

13% water as a solvent;
6.7% Trilube 112, which is a coconut methyl ester, as the shorter chain aliphatic compound;
80% of a palm methyl ester, which contains a mixture of longer chain aliphatic and complex compounds; and
0.3% of an emulsifier.

Example 2

In this example a small percentage of a redispersable polymer powder is introduced to assist with the blending of urea particles with other granular fertilizers (SSP as an example). In such example the composition typically comprises (w/w):

- 22% water as a solvent;
- 16.5% lauryl alcohol as the shorter chain aliphatic compound;
- 58% of a mixed methyl ester, which contains a mixture of longer chain aliphatic and complex compounds;
- 3% of a redispersable polymer powder; and
- 0.5% of an emulsifier.

Example 3

It may be desired to accelerate the curing or formation of the urea clathrate without compromising the strength of the clathrate significantly. This is accomplished by reducing the percentage of the longer chain aliphatic compounds as well as the emulsifier and introducing a larger percentage of the shorter chain and mid-length aliphatic compounds. Such a composition typically comprises (w/w):

- 16% water as a solvent;
- 26% coconut methyl ester as the shorter chain aliphatic compound;
- 36% of a tallow methyl ester, which contains a mixture of longer chain aliphatic and complex compounds;
- 18% of a hydrogenated palm methyl ester containing $C_{17}$ aliphatic hydrocarbon chains;
- 1% of a polyethylene glycol dispersing agent; and
- 3% of a humic acid.

Example 4

It may occasionally be desired to have the urea clathrate boundary layer be relatively rigid but be able to display a certain flexibility over time so that it is able to expand and contract together with any such expansion or contraction exhibited by the urea particle without the boundary layer becoming damaged. This is achieved through the addition of complex aliphatic chains into the composition. Such a composition typically comprises (w/w):

- 20.5% water as a solvent;
- 27.45% coconut methyl ester as the shorter chain aliphatic compound;
- 26% flax seed containing complex compounds;
- 26% of a hydrogenated palm methyl ester containing $C_{17}$ aliphatic hydrocarbon chains;
- 0.05% of an emulsifier.

Example 5

An additional trace element or micro particle nutrient component may be introduced to the composition. This nutrient component (e.g. sulphur) is entrapped in the urea clathrate boundary layer as it forms on the surface of the urea particles. The nutrient can vary depending on the need. Such a composition typically comprises (w/w):

- 15% water as a solvent;
- 19% coconut methyl ester as the shorter chain aliphatic compound;
- 58% of a mixed methyl ester, which contains a mixture of longer chain aliphatic and complex compounds;
- 1.5% of a polyethylene glycol dispersing agent; and
- 6.5% nano sulphur particles.

It will be appreciated by persons skilled in the art that numerous variations and/or modifications may be made to the disclosure as shown in the examples without departing from the spirit or scope of the disclosure as broadly described. The present embodiments are, therefore, to be considered in all respects as illustrative and not restrictive.

In the claims which follow and in the preceding description, except where the context requires otherwise due to express language or necessary implication, the word "comprise" or variations such as "comprises" or "comprising" is used in a non-limiting and an inclusive sense, i.e. to specify the presence of the stated features but not to preclude the presence or addition of further features in the various embodiments of the crusher. A reference to an element by the indefinite article "a" does not exclude the possibility that more than one of the elements is present, unless the context clearly requires that there be one and only one of the elements.

The invention claimed is:

1. A composition for treating urea particles, the composition comprising:
    water as a polar solvent;
    a first aliphatic compound of the formula $$R^1-[CH_2]_n-R^2$$

wherein
    $R^1$ is hydrogen or a first terminal functional group;
    $R^2$ is hydrogen or a second terminal functional group; and
    n is 8 to 14; and
    a second aliphatic compound of the formula $$H-[CH_2]_n-R$$

wherein
    R is hydrogen or a hydroxyl group or a carboalkoxy group or a carboxyl group; and
    n is 15 to 19;
        wherein, the composition is configured to be applied to urea particles under ambient atmospheric conditions to form a barrier layer comprising a urea clathrate that at least partially encloses the urea particles so that moisture induced agglomeration of urea particles treated with the composition is reduced compared to moisture induced agglomeration of untreated urea particles.

2. The composition as claimed in claim 1, wherein the water comprises between 10%-30% (w/w) of the composition.

3. The composition as claimed in claim 1, wherein the first and second terminal functional group are selected from the group of hydroxyl, carboalkoxy and carboxyl functional groups.

4. The composition as claimed in claim 1, wherein the first aliphatic compound is an alcohol selected from the group of 1-octanol, 1-nonanol, 1-decanol, 1-undecanol, 1-dodecanol, 1-tridecanol, and 1-tetradecanol.

5. The composition as claimed in claim 4, wherein the first aliphatic compound is 1-dodecanol.

6. The composition as claimed in claim 1, wherein the first aliphatic compound is an ester selected from the group of octyl acetate and dodecyl acetate.

7. The composition as claimed in claim 1, wherein the first aliphatic compound is a carboxylic acid selected from the group of octanoic, nonanoic, decanoic, undecanoic, dodecanoic, and tridecanoic acid.

8. The composition as claimed in claim 1, wherein the first aliphatic compound is an ester selected from the group of methyl, ethyl, and propyl esters of any of the saturated, un-branched carboxylic acids selected from the group of octanoic, nonanoic, decanoic, undecanoic, dodecanoic, and tridecanoic acid.

9. The composition as claimed in claim 1, wherein the second aliphatic compound is a methyl ester which is comprised in a mixture of methyl esters, a palm methyl ester or a tallow methyl ester.

10. The composition as claimed in claim 9, wherein the mixture of methyl esters is selected from the group of a biodiesel, recycled cooking oils and recycled cooking fats.

11. The composition as claimed in claim 9, wherein the mixture of methyl esters, the palm methyl ester or the tallow methyl ester comprises
30-40% (w/w) of the second aliphatic compound; and
60-70% (w/w) of unsaturated esters, branched chain esters and aromatic esters.

12. The composition as claimed in claim 1, which comprises
15-20% (w/w) of the water;
5-20% (w/w) of the first aliphatic compound; and
60-80% (w/w) of the second aliphatic compound wherein the second aliphatic compound is a methyl ester which is comprised in a mixture of methyl esters.

13. The composition as claimed in claim 1, which comprises 0-1% (w/w) of an emulsifier or 0-2% (w/w) of a dispersing agent.

14. A method of treating urea particles, the method comprising the steps of:
a) dosing a supply of urea particles with an amount of a liquid composition effective for reducing moisture induced agglomeration of the urea particles, wherein the liquid composition includes
water as a polar solvent,
a first aliphatic compound of the formula

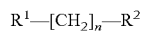

wherein
$R^1$ is hydrogen or a first terminal functional group;
$R^2$ is hydrogen or a second terminal functional group; and
n is 8 to 14, and
a second aliphatic compound of the formula

wherein
R is hydrogen, a hydroxyl group or a carboalkoxy group or a carboxyl group; and
n is 15 to 19;

b) mixing the urea particles and the liquid composition under ambient atmospheric conditions at a temperature of 15-40° C. and a humidity of 30-90% to promote coating of the urea particles with the liquid composition, whereby the liquid composition is configured to form a barrier layer comprising a urea clathrate that at least partially encloses the urea particles; and
c) allowing the urea clathrate to cure under the ambient atmospheric conditions for a time period of 30-120 seconds, thereby forming treated urea particles.

15. The method as claimed in claim 14, comprising the step of selectively altering the ratio between the water, the first aliphatic compound and the second aliphatic compound, thereby to adjust a rate of curing of the urea clathrate.

16. The method as claimed in claim 14, wherein the urea particles are dosed with the liquid composition at a ratio of about 5-15 kg of liquid composition per 1000 kg of urea particles.

17. The method as claimed in claim 14, wherein the urea particles are dosed with the liquid composition at a ratio of about 7.5-10 kg of liquid composition per 1000 kg of urea particles.

18. The method as claimed in claim 14, wherein, when the urea particles are to be blended with other solid fertilisers, the urea particles are dosed with the liquid composition at a ratio of about 10-15 kg of liquid composition per 1000 kg of urea particles.

19. The method as claimed in claim 14, wherein the urea clathrate is allowed to cure for a time period of 45-75 seconds under ambient atmospheric conditions.

20. The method as claimed in claim 14, wherein selective trace elements or micro particles are added to the urea particles during step (a) or step (b) so that the treated urea particles formed during step (c) comprise selective trace elements or micro particles entrapped within the urea clathrate.

21. The method as claimed in claim 20, wherein the trace elements or micro particles are selected from the group of
nano-particles of zinc oxide, copper oxide, lime, and elemental sulphur;
humic and/or fulvic acid;
lignins;
redispersable polymer powders; and
(n-butyl) thiophosphoric triamide (NBPT).

22. The method as claimed in claim 14, wherein the urea particles are treated after being manufactured, after being off-loaded from a bulk transport, or prior to being distributed or bagged for distribution to down-chain wholesalers, retailers or consumers.

* * * * *